United States Patent
Yamamoto et al.

(10) Patent No.: US 7,208,627 B2
(45) Date of Patent: Apr. 24, 2007

(54) ALKYLBORAZINE COMPOUND AND PRODUCTION METHOD FOR THE SAME

(75) Inventors: Tetsuya Yamamoto, Nishinomiya (JP); Yasutaka Nakatani, Higashiosaka (JP); Takuya Kamiyama, Takatsuki (JP)

(73) Assignee: Nippon Shokubai Co., Ltd, Osaka (JP)

( * ) Notice: Subject to any disclaimer, the term of this patent is extended or adjusted under 35 U.S.C. 154(b) by 160 days.

(21) Appl. No.: 11/013,192

(22) Filed: Dec. 15, 2004

(65) Prior Publication Data

US 2005/0177002 A1  Aug. 11, 2005

(30) Foreign Application Priority Data

Dec. 18, 2003 (JP) ............... 2003-420747
Feb. 19, 2004 (JP) ............... 2004-043112

(51) Int. Cl.
*C07F 5/02* (2006.01)

(52) U.S. Cl. ..................... 564/10; 260/665 G
(58) Field of Classification Search ............... 564/10; 260/665 G
See application file for complete search history.

(56) References Cited

U.S. PATENT DOCUMENTS

2002/0058142 A1  5/2002  Tsunoda et al. ......... 428/411.1
2003/0100175 A1  5/2003  Nobutoki et al. ........... 438/623

FOREIGN PATENT DOCUMENTS

JP  2003-119289  4/2003

OTHER PUBLICATIONS

Ryschkewitsch et al., The Chemistry of Borazene. I. The Reaction of B-Trichloro-N-trimethylborazene with Grignard Reagents1, J. Am. Chem. Soc.; 1958; 80(17); 4515-4517.*
Grace et al., Borazines. III. Some Reactions of B-Tri-N-alkylborazines with Grignard Reagents, J. Chem. Soc A: Inorganic, Physical, Theoretical; 1966; (6); 673-676.*

Haworth, D.T. and Hohnstedt, L.F., "Synthesis of B-Trisubstituted Borazines by Reaction of B-Trichloroborazine With Grignard Reagents", J. Am. Chem. Soc., 82, 3860-3861 (1960).

* cited by examiner

*Primary Examiner*—Thurman K. Page
*Assistant Examiner*—Chukwuma Nwaonicha
(74) *Attorney, Agent, or Firm*—Mathhews, Shepherd, McKay & Bruneau, P.A.

(57) ABSTRACT

In the process of synthesizing alkylborazine compound represented by the chemical formula 2, by a reaction of a halogenated borazine compound represented by the chemical formula 1 with a Grignard reagent, thus synthesized alkylborazine compound is washed with water, or subjected to sublimation purification or distillation purification at least three times, and/or subjected to distillation purification at least twice. In the formulas, $R^1$ independently represents alkyl group; $R^2$ independently represents alkyl group; and X represents halogen atom.

[chemical formula 1]

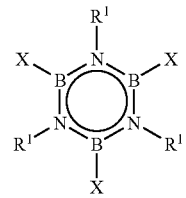

[chemical formula 2]

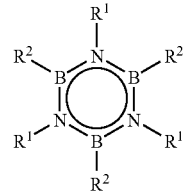

7 Claims, No Drawings

ALKYLBORAZINE COMPOUND AND PRODUCTION METHOD FOR THE SAME

BACKGROUND OF THE INVENTION

1. Field of the Invention

The present invention relates to alkylborazine compound. Alkylborazine compound is used to form, for example, an interlayer dielectric film for semiconductor, a barrier metal layer and an etching stopper layer.

2. Description of Related Art

With higher functionalization of information devices, design rule of LSI has been required to be finer year by year. In production of LSI with finer design rule, materials composing LSI should also have higher performance and fulfill function even on fine LSI.

For example, as for materials used for an interlayer dielectric film in LSI, high dielectric constant causes signal delay. In fine LSI, effects of the signal delay is particularly significant. Therefore, development of a new low dielectric material which can be used for an interlayer dielectric film has been needed. Also to be used as an interlayer dielectric film, it is necessary not only to have low dielectric constant but also superior characteristics such as humidity resistance, heat resistance, mechanical strength, etc.

As a material to respond to these requirements, a compound having borazine ring backbone has been proposed (for example, see U.S. patent publication No. 2002-58142). A compound having borazine ring backbone has small molecular polarizability and thus a coated membrane formed provides low dielectric constant. Moreover, the coated membrane formed is superior in heat resistance.

As a borazine-ring containing compound, various compounds have been proposed up to now. For example, alkylborazine compound, whose boron moiety is substituted with alkyl group, has very superior characteristics as a low dielectric material (for example, see JP-2003-119289A). Alkylborazine compound, whose boron moiety is substituted with alkyl group, can be synthesized by preparing B,B',B''-trichloro-N,N',N''-trialkylborazine such as B,B',B''-trichloro-N,N',N''-triethylborazine as a raw material, and by substituting a chlorine atom of the compound with alkyl group by using a Grignard reagent (for example, see D. T. HAWORTH and L. F. HOHNSTEDT, J. Am. Chem. Soc., 82, 3860 (1960)).

Alkylborazine compound synthesized is purified in response to usage after synthesis. As purification methods, sublimation purification, wherein a mixture is separated utilizing difference in sublimation temperature specific to a compound, and distillation purification, wherein a mixture is separated utilizing difference in boiling temperature specific to a compound are known.

BRIEF SUMMARY OF THE INVENTION

By known purification methods such as sublimation purification and distillation purification, alkylborazine compound with purity to certain degree can be obtained. However, development of a purification method is required to obtain alkylborazine compound with further high purity. In particular, it is required that contamination amount of metal elements or halogen elements is very low when it is applied to semiconductor materials.

In this connection, the present inventors have found that trialkylborane, which is generated as a byproduct in a purified alkylborazine compound, may raise various problems.

Trialkylborane is an unstable compound and has high ignitability. Ttrialkylborane also has lower boiling point compared with an objective product, alkylborazine compound, and thus ignition may easily occur by trialkylborane diffused in atmosphere. It is not clear at present that natural ignition is caused by how much quantity of trialkylborane present in atmosphere. Further, alkylborazine compound produced by a conventional technology is not necessarily a dangerous compound. However, it is preferable that such a compound is removed at most, in view of safety for workers or facility.

Therefore, an object of the present invention is to provide a production method for alkylborazine compound having very low contamination level of impurity such as metal elements, halogen elements, trialkylborane, etc.

In an aspect of the invention, a method for production of alkylborazine compound includes steps of synthesizing an alkylborazine compound represented by the chemical formula 2 by a reaction of a halogenated borazine compound represented by the chemical formula 1 with a Grignard reagent; and washing the synthesized alkylborazine compound with water:

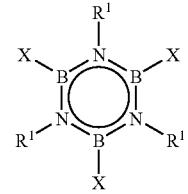

[chemical formula 1]

wherein $R^1$ independently represents alkyl group; and X represents halogen atom,

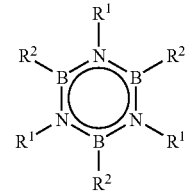

[chemical formula 2]

wherein $R^1$ independently represents alkyl group; and $R^2$ independently represents alkyl group.

In another aspect of the invention, instead of or in addition to the washing step with water, such a step may be adopted, wherein thus synthesized alkylborazine compound is subjected to sublimation purification or distillation purification at least three times.

In still another aspect of the invention, instead of or in addition to the washing step with water, such a step may also be adopted, wherein thus synthesized alkylborazine compound is subjected to distillation purification at least twice.

By the present invention, alkylborazine compound with very small amount of impurity contamination can, be produced.

DETAILED DESCRIPTION OF THE INVENTION

The present invention relates to a method for production of alkylborazine compound includes a step of synthesizing an alkylborazine compound represented by the chemical formula 2, by a reaction of a halogenated borazine compound represented by the chemical formula 1 with a Grignard reagent:

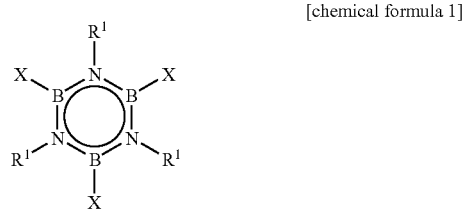

[chemical formula 1]

wherein $R^1$ independently represents alkyl group; and X represents halogen atom,

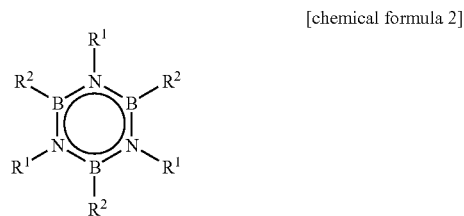

[chemical formula 2]

wherein $R^1$ independently represents alkyl group; and $R^2$ independently represents alkyl group.

In producing alkylborazine compound represented by the chemical formula 2 using a halogenated borazine compound represented by the chemical formula 1 as a raw material, a residual halogenated borazine compound is included in a reaction system in addition to an objective compound, alkylborazine compound. It is preferable that compounds other than alkylborazine compound are removed using a purification method such as sublimation purification and distillation purification. However, a halogenated borazine compound and alkylborazine compound have similar property, which inhibits efficient purification. For example, when alkylborazine compound is purified using sublimation purification, separation efficiency is lowered because sublimation temperature of a halogenated borazine compound and sublimation temperature of alkylborazine compound are quite near.

One of a method to reduce impurity includes washing of a synthesized alkylborazine compound with water. Up to now, a borazine compound has been considered to have low water resistance and decomposed when contacted with water (see, for example, Earl L. Muetterties, "BORON HYDRIDE CHEMISTRY", ACADEMIC PRESS, p. 257–259). In reality, a halogenated borazine compound represented by the chemical formula 1 is decomposed when contacted with water. However, such a fact was discovered by the inventers of the present invention that alkylborazine compound represented by the chemical formula 2 is hardly decomposed even by contact with water. In the present invention, based on such knowledge, a synthesized halogenated borazine compound is washed with water. By water for washing, a halogenated borazine compound, that is impurity, is decomposed. While, an objective compound, alkylborazine compound, remains as a whole or in most part. Property of decomposed fractions of a halogenated borazine compound differs largely from that of alkylborazine compound. Therefore impurities derived from a halogenated borazine compound can be efficiently separated by means of a purification method such as sublimation purification or distillation purification and alkylborazine compound with very small impurity content can be produced.

Another method to reduce impurity includes at least three times of repetition of sublimation purification or distillation purification. It is known that purity is increased by purification of a synthesized compound. However, the present inventors have found that in purification of alkylborazine compound, impurity which can not sufficiently be removed by a first purification or a second purification can dramatically be removed by a third purification. Mechanism of the above, that is, "impurity which can not sufficiently be removed by the first purification or the second purification can be dramatically removed by the third purification", is not clarified at present. However, as shown by Examples of the present invention, significant effect is obtained by the third purification.

Another method to reduce impurity includes a step of removing trialkylborane by repeating distillation purification at least twice.

Generation mechanism of trialkylborane having ignitability is not clear but the following mechanism is estimated.

Alkylborazine compound represented by the chemical formula 2 is synthesized by a reaction of a halogenated borazine compound represented by the chemical formula 1 with a Grignard reagent. However, yield of the reaction between a halogenated borazine compound and a Grignard reagent is generally not so high, therefore, certain amount of a Grignard reagent remains in a solution after the reaction. Thus remained Grignard reagent reacts with a synthesized alkylborazine compound, resulting in formation of trialkylborane. When a composition containing alkylborazine compound and a remaining Grignard reagent is heated for purification, the reaction between alkylborazine compound and a Grignard reagent proceeds more fiercely and thus much more quantities of trialkylborane are generated.

If it is aimed only to suppress the reaction between alkylborazine compound and a Grignard reagent, it may be enough to reduce use amount of a Grignard reagent. However, boiling temperature of halogenated borazine compound, a raw material, and boiling temperature of alkylborazine compound, an objective material, are generally very near, which makes purification very difficult when unreacted halogenated borazine compounds remain. Consequently, to suppress unreacted halogenated borazine compounds at most, it is inevitable to use a Grignard reagent in certain amounts.

Trialkylborane can effectively be removed by subjecting alkylborazine compound to distillation purification at least twice.

In a composition after a Grignard reaction, an objective compound, alkylborazine compound and an unreacted Grignard reagent are contained. First of all, this composition is subjected to distillation purification. By the first distillation purification, a Grignard reagent is removed. However, as described above, an unreacted Grignard reagent and alkylborazine compound are reacted and trialkylborane is generated. In particular, heat added in distillation purification accelerates a generation reaction of trialkylborane.

Usually, distillation purification is performed only once and distillation purification is not repeated twice or more. The present inventors have studied on removal of trialkylborane and found out that the second distillation purification is useful to remove trialkylborane. By the first distillation purification, a Grignard reagent itself can be removed, however, as described above, by a reaction between an unreacted Grignard reagent and alkylborazine compound, trialkylborane is generated which remains in a composition after distillation in certain amount. In the present invention, trialkylborane contained in a composition after first distillation can be removed by the second distillation purification. As the result, in a composition after the second distillation purification, a highly safe alkylborazine compound with supremely low content of trialkylborane, which otherwise may cause lower safety, is provided.

When purification is repeated twice or more, meaning of the first purification and the second purification differs. The first distillation purification is purification to remove impurity such as a Grignard reagent, while, the second purification is purification to remove trialkylborane generated accompanied with the first purification. Here, transition of major components is briefly explained as follows: "a halogenated borazine compound+a Grignard reagent" (raw materials)→"alkylborazine compound+remained Grignard reagent" (after a Grignard reaction)→"alkylborazine compound+trialkylborane" (after the first distillation purification) →"alkylborazine compound" (after the second distillation purification). Only major components are listed above for explanation purpose and therefore embodiments including other components are not excluded from technical scope of the present invention.

The present invention is now explained in more detail.

First of all, a halogenated borazine compound used as a raw material, represented by the chemical formula 1, is prepared.

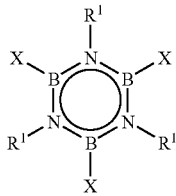

[chemical formula 1]

In the formula, $R^1$ may be the same or different. When yield of a synthesis reaction or handling easiness is considered, $R^1$ is preferably the same alkyl group. Alkyl group may be straight, branched or cyclic. Carbon number in alkyl group is not especially limited, however, preferably 1 to 8, more preferably 1 to 4 and further preferably 1. A specific example of alkyl group includes methyl group, ethyl group, propyl group, iso-propyl group, butyl group, iso-butyl group, sec-butyl group, tert-butyl group, pentyl group, iso-pentyl group, neo-pentyl group, hexyl group, heptyl group, octyl group, nonyl group, decyl group, cyclopropyl group, cyclopentyl group, cyclohexyl group, etc. Alkyl group other than these may also be used.

An example of a halogenated borazine compound includes
B,B',B"-trichloro-N,N',N"-trimethylborazine,
B,B',B"-trichloro-N,N',N"-triethylborazine,
B,B',B"-trichloro-N,N',N"-tri(n-propyl)borazine,
B,B',B"-trichloro-N,N',N"-tri(iso-propyl)borazine,
B,B',B"-trichloro-N,N',N"-tri(n-butyl)borazine,
B,B',B"-trichloro-N,N',N"-tri(sec-butyl)borazine,
B,B',B"-trichloro-N,N',N"-tri(iso-butyl)borazine,
B,B',B"-trichloro-N,N',N"-tri(tert-butyl)borazine,
B,B',B"-trichloro-N,N',N"-tri(1-methylbutyl)borazine,
B,B',B"-trichloro-N,N',N"-tri(2-methylbutyl)borazine,
B,B',B"-trichloro-N,N',N"-tri(neo-pentyl)borazine,
B,B',B"-trichloro-N,N',N"-tri(1,2-dimethylpropyl)borazine,
B,B',B"-trichloro-N,N',N"-tri(1-ethylpropyl)borazine,
B,B',B"-trichloro-N,N',N"-tri(n-hexyl)borazine and
B,B',B"-trichloro-N,N',N"-tricyclohexylborazine.

They may be substituted by other halogen elements such as in
B,B',B"-trifluoro-N,N',N"-trimethylborazine,
B,B',B"-tribromo-N,N',N"-trimethylborazine,
B,B',B"-monochlorodifluoro-N,N',N"-trimethylborazine, etc.

A method to obtain a halogenated borazine compound is not especially limited. In synthesis of a halogenated borazine compound, known knowledge may be referred to, as appropriate. For example, a synthesis method described in "D. T. HAWORTH, Inorganic Syntheses, 10, 43(1971)" may be adopted. When synthesized in one's own, for example, boron trichloride ($BCl_3$) and an amine compound represented by the following chemical formula 3 are reacted. A reaction between boron trichloride and an amine compound is preferably a reaction wherein boron trichloride is added to an amine compound suspended in a solvent. As a solvent here, o-xylene, m-xylene, p-xylene, monochlorobenzene, o-dichlorobenzene, m-dichlorobenzene, and the like may be used. Ambient atmosphere of a reaction solution is not especially limited, however, ambient atmosphere of a reaction solution is preferably replaced with inert gas such as nitrogen and argon.

$$R^3HN_3X$$ [Chemical Formula 3]

In the amine compound represented by the chemical formula 3, $R^3$ is alkyl group. Alkyl group may be straight, branched or cyclic. Carbon number in alkyl group is not especially limited, however, preferably 1 to 8, more preferably 1 to 4 and further preferably 1. A specific example of alkyl group includes methyl group, ethyl group, propyl group, iso-propyl group, butyl group, iso-butyl group, sec-butyl group, tert-butyl group, pentyl group, iso-pentyl group, neo-pentyl group, hexyl group, heptyl group, octyl group, nonyl group, decyl group, cyclopropyl group, cyclopentyl group, cyclohexyl group, etc. Alkyl group other than these may also be used. X is halogen atom, specifically, fluorine atom, chlorine atom, bromine atom or iodine atom. X is preferably chlorine atom in view of easy availability of a raw material and high reactivity.

A halogenated borazine compound thus prepared is reacted with a Grignard reagent, resulting in synthesis of alkylborazine compound represented by the chemical formula 2. A reaction to substitute a halogen atom of a halogenated borazine compound with alkyl group by a reaction between a halogenated borazine compound and a Grignard reagent, is only briefly explained below because it is a known reaction as is shown at D. T. HAWORTH and L. F. HOHNSTEDT, J. Am. Chem. Soc., 82, 3860 (1960), etc.

A Grignard reaction induced by a Grignard reagent, represented by, for example, $R^4MgX$ type (wherein $R^4$ represents alkyl group and X represents halogen atom), substitutes a halogen atom contained in a specified compound with alkyl group contained in a Grignard reagent. As for a halogenated borazine compound, a halogen atom directly bonded to boron is substituted with alkyl group contained in a Grignard reagent.

As for a Grignard reagent, various types such as $CH_3MgI$, $CH_3CH_2MgBr$, $CH_3CH_2CH_2MgI$, and the like can be used. The Grignard reagent is not limited to these.

Reaction conditions between a Grignard reagent and a halogenated borazine compound is not especially limited. For example, under nitrogen atmosphere, a specific halogenated borazine compound and diether as a solvent are fed into a reactor. And, $CH_3MgI$ as a Grignard reagent is gradually dropped to this reaction solution, while stirring the reaction solution.

As for the addition amount of a halogenated borazine compound and a Grignard reagent, if a halogenated borazine compound is used more than stoichiometric ratio, it is possible to reduce a Grignard reagent remained after the reaction. However, because boiling temperature of a halogenated borazine compound and boiling temperature of alkylborazine compound are quite near, distillation may become difficult. While, if a Grignard reagent is used more than stoichiometric ratio, it is possible to reduce a halogenated borazine compound remained after the reaction. However, by a Grignard reagent remaining in high quantity, generation of trialkylborane may be accelerated. In addition, magnesium or halogen elements derived from a Grignard reagent may be included in high quantity as impurities. In view of these, while a Grignard reagent is dropped preferably to an amount a little over theoretically required level in a general Grignard reaction, a Grignard reagent in a stoichiometric ratio range of 0.7 to 1.3 based on use amount of a halogenated borazine compound as 1.0 may be used. By setting use amount of a Grignard reagent within such a range, impurities in alkylborazine compound derived from a Grignard reagent, such as halogen elements including Br or Cl, metal elements including Mg, and the like can effectively be reduced.

Alkylborazine compound produced has structure represented by chemical formula 2. "Alkylborazine compound" in the present invention means a compound represented by the chemical formula 2 unless otherwise noted.

[chemical formula 2]

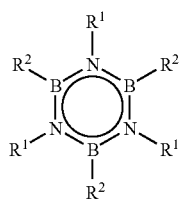

In the formula, $R^1$ represents alkyl group. $R^1$ in alkylborazine compound may be the same or different. $R^1$ is a group derived from $R^1$ in the chemical formula 1. Explanation on $R^1$ is omitted here because it is as explained on $R^1$ in the chemical formula 1.

$R^2$ is alkyl group derived from a Grignard reagent. When a Grignard reagent is expressed by $R^4MgX$, $R^2$ is alkyl group derived from $R^4$. Structure of alkylborazine compound is not especially limited, however, in view of property when used as a semiconductor material, $R^1$ and $R^2$ are preferably both alkyl groups. That is, alkylborazine compound is preferably hexaalkylborazine.

A specific example of hexaalkylborazine includes hexamethylborazine, hexaethylborazine, hexa(n-propyl)borazine, hexa(iso-propyl)borazine, hexa(n-butyl)borazine, hexa(sec-butyl)borazine, hexa(iso-butyl)borazine, hexa(tert-butyl)borazine, hexa(1-methylbutyl)borazine, hexa(2-methylbutyl)borazine, hexa(neo-pentyl)borazine, hexa(1,2-dimethylpropyl)borazine, hexa(1-ethylpropyl)borazine, hexa(n-hexyl)borazine, hexacyclohexylborazine, B,B',B"-trimethyl-N,N',N"-triethylborazine, B,B',B"-trimethyl-N,N',N"-tri(n-propyl)borazine, B,B',B"-trimethyl-N,N',N"-tri(iso-propyl)borazine, B,B',B"-triethyl-N,N',N"-trimethylborazine, B,B',B"-triethyl-N,N',N"-tri(n-propyl)borazine, B,B',B"-triethyl-N,N',N"-tri(iso-propyl)borazine, B,B',B"-tri(iso-propyl)-N,N',N"-trimethylborazine, B,B',B"-tri(iso-propyl)-N,N',N"-triethylborazine, etc.

In the first aspect of the present invention, alkylborazine compound synthesized is washed with water. Alkylborazine compound is washed with water preferably containing metal elements not higher than 1 ppb and halogen elements not higher than 0.5 ppm, more preferably metal elements not higher than 0.1 ppb and halogen elements not higher than 0.05 ppm. When a reaction product is washed with water, it generally aims at removing water soluble impurities. In the present invention, washing water is used to decompose impurities. However, removal of water soluble impurities by water may be aimed at simultaneously. For example, impurity metal elements may be dissolved out in water as ions and may be removed from alkylborazine compound.

When alkylborazine compound is washed with water, washing embodiments are not especially limited as long as a halogenated borazine compound contained in alkylborazine compound can be decomposed. For example, alkylborazine compound is washed by using a separatory funnel fed with an organic solvent such as toluene dissolved with a solid substance containing alkylborazine compound obtained and ion exchanged water. The amount of used washing water may be determined in response to the amount of alkylborazine compound to be washed and washing embodiments.

In the first aspect of the present invention, as long as a purification of alkylborazine compound synthesized adopts at least a step of washing alkylborazine compound with water, other steps are not especially limited. As long as at least a washing step of alkylborazine compound is present and a halogenated borazine compound as impurity is decomposed, it is included as technical scope of the present invention. For example, alkylborazine compound synthesized is subjected to three steps including washing, the first sublimation purification and the second sublimation purification. In this case, by washing with water, a halogenated borazine compound is tried to be decomposed. Then, by repeating sublimation purification, a high purity alkylborazine compound can be obtained. Depending on the case, distillation purification may be used instead of sublimation purification. When alkylborazine compound is washed with water, followed by sublimation purification or distillation purification, efficiency in sublimation purification or distillation purification can be improved by decomposition of alkylborazine compound via washing with water.

In the second aspect of the present invention, after synthesis of alkylborazine compound by a reaction between a halogenated borazine compound and a Grignard reagent, at least three times of sublimation purification or distillation purification are repeated. Explanation on a synthesis step of alkylborazine compound by a reaction between a halogenated borazine compound and a Grignard reagent is omitted because it is similar to explanation in the first aspect of the present invention.

Purification may adopt both sublimation purification and distillation purification. In the present invention, "at least three times of sublimation purification or distillation purification" means that total number of sublimation purification and distillation purification is three times or more. Thus, only one of sublimation purification or distillation purification may be adopted. That is, alkylborazine compound may be purified by at least three times of sublimation purification or at least three times of distillation purification or at least three times of sublimation purification and distillation purification in combination.

Sublimation purification is a purification method to separate impurity and objective compound by utilization of difference in sublimation temperature of compounds. Embodiments of sublimation purification are not especially limited, and style of sublimation purification equipment may be selected, as appropriate, in response to production scale of alkylborazine compound or production environment. By strict temperature control by gas flow, purity of objective compound obtained can be improved. Distillation purification is a purification method to separate impurity and objective compound by distillation by utilization of difference in volatility of each component. Embodiments of distillation purification are also not especially limited and knowledge obtained up to now may be used as references.

In the third aspect of the present invention, a composition containing alkylborazine compound synthesized by a reaction between a halogenated borazine compound and a Grignard reagent is subjected to at least twice of distillation purification. By distillation purification, a highly safe alkylborazine compound having very low content of trialkylborane can be obtained.

Technique of distillation purification in the third aspect of the present invention is not especially limited, as long as it can separate an objective compound, a halogenated borazine compound, a Grignard reagent and trialkylborane. To obtain the effect of the present invention, it is enough if a halogenated borazine compound and a Grignard reagent can be separated in the first distillation purification and a halogenated borazine compound and trialkylborane can be separated in the second distillation purification. Before distillation purification, general treatment in the field of organic synthesis may be performed. For example, a reaction solution may be filtered and concentrated using an evaporator.

Scale and type of distillation purification equipment may be determined in response to environment or scale, which the present invention is applied to. For example, to handle a large quantity of a composition, an industrial scale distillation tower may be used. While, to treat small quantity of a compound, distillation purification using a distillation tube can be used. For example, as a specific example of equipment for distillation purification to deal with a small quantity of composition, distillation equipment attached with a Liebig condenser by a Claisen type connecting tube to a 3-neck flask may be used. However, technical scope of the present invention is by no means limited to practice embodiments using these equipments for distillation purification.

Alkylborazine compound obtained by a production method of the present invention contains impurity at a quite low level. Specifically, alkylborazine compound of the present invention preferably contains halogen elements not higher than 1 ppm. Alkylborazine compound of the present invention also preferably has metal content not higher than 100 ppb. These values are calculated based on weight of alkylborazine compound. Lower content limit of halogen elements and metals is not especially limited. Because they are impurities, they are preferably as low as possible, in general. When multiple halogen elements or metal elements are contained, it is preferable that a total amount thereof falls within the above range.

Halogen elements can be present as contaminants in alkylborazine compound by various reasons. Major sources include halogen elements contained in a halogenated borazine compound and halogen elements contained in a Grignard reagent. For example, when B,B',B''-trichloro-N,N',N''-trimethylborazine is used as a halogenated borazine compound, a chlorine atom is mixed in alkylborazine compound. And also when methyl magnesium bromide is used as a Grignard reagent, a bromine atom is mixed in alkylborazine compound.

A halogen element mixed in alkylborazine compound can be measured by using ion chromatography. Types of ion chromatography and measurement conditions are not especially limited. When measured value differs depending on instrument used or measurement conditions, value measured by a method described in Examples is adopted as metal content.

Metals can be contaminated in alkylborazine compound by various reasons. Major source includes metal elements contained in a Grignard reagent. For example, when methyl magnesium bromide is used as a Grignard reagent, magnesium is mixed in alkylborazine compound.

Metals mixed in alkylborazine compound can be measured by using an inductively coupled plasma emission spectrometer (ICP). Types of ICP and measurement conditions are not especially limited. When measured value differs depending on instrument used or measurement conditions, value measured by a method described in Examples is adopted as metal content.

Alkylborazine compound obtained by a production method of the present invention preferably has, after completion of distillation purification, content of trialkylborane in alkylborazine compound not higher than 1 ppm. When the content of trialkylborane can be reduced to not higher than 1 ppm, safety can be improved to very high level. The content of trialkylborane is calculated based on weight of trialkylborane. Lower content limit of trialkylborane is not especially limited, however, it is preferably as low as possible, in general.

Ttrialkylborane removed by distillation purification is a compound represented by the chemical formula 4:

$$R^5{}_3B$$  [Chemical Formula 4]

In the formula, $R^5$ is alkyl group. $R^5$ in trialkylborane may be the same or different. Alkyl group may be straight, branched or cyclic. A specific example of alkyl group includes methyl group, ethyl group, propyl group, iso-propyl group, butyl group, iso-butyl group, sec-butyl group, tert-butyl group, pentyl group, iso-pentyl group, neo-pentyl group, hexyl group, heptyl group, octyl group, nonyl group, decyl group, cyclopropyl group, cyclopentyl group and cyclohexyl group, etc. Alkyl group other than these may be used. A specific example of trialkylborane includes trimethylborane, triethylborane, tripropylborane, ethyldimethylborane, etc. Practically generated trialkylborane depends on types of a Grignard reagent used. For example, when $CH_3CH_2MgBr$ is used as a Grignard reagent, triethylborane $((CH_3CH_2)_3B)$ can be generated.

Trialkylborane mixed in alkylborazine compound can be measured by using gas chromatography-mass spectrometer (GC-MS). Types of measurement instrument and measurement conditions are not especially limited, as long as data having statistically constant certainty can be obtained. When measured value differs depending on instrument used or measurement conditions, value measured by a method described in Examples is adopted as content of trialkylborane.

Applications of alkylborazine compound produced are not especially limited. It is used to form an interlayer dielectric film for semiconductor, a barrier metal layer, an etching stopper layer, etc. For these applications, alkylborazine compound may be used as it is, or a compound obtained by modification of alkylborazine compound may also be used. A polymer obtained by polymerization of alkylborazine compound or derivatives thereof may be used as a raw material for an interlayer dielectric film for semiconductor, a barrier metal layer, an etching stopper layer.

A polymer may be formed by using a borazine-ring containing compound as a monomer. A polymerization method or polymerization type is not especially limited. A polymerization method may be selected in response to a functional group bonded to a borazine ring. For example, an amino group is bonded, a polymer may be synthesized by polycondensation. When a vinyl group or a vinyl-containing functional group is bonded to a borazine ring, a polymer may be formed by radical polymerization using a polymerization initiator. A polymer may be a homopolymer or a copolymer containing two or more monomer units. Copolymer morphology may be any of a random copolymer, a block copolymer or a graft copolymer. By using a monomer having three or more functional groups capable of forming a bond with other monomer, a network-like bonded polymer can be obtained.

Now, a method for forming an interlayer dielectric film for semiconductor, a barrier metal layer or an etching stopper layer is explained. In the following explanation, "alkylborazine compound", "derivatives of alkylborazine compound" and "a polymer induced from these" are named as "a borazine-ring containing compound".

To form an interlayer dielectric film for semiconductor, a barrier metal layer or an etching stopper layer using a borazine-ring containing compound, a solution or slurry-like composition containing a borazine-ring containing compound is first prepared. And, a coated film is formed by coating the solution or the composition. A solvent used here to dissolve or disperse a borazine-ring containing compound is not especially limited, as long as it can dissolve or disperse a borazine-ring containing compound or other components added if necessary. A solvent here includes, for example, alcohols such as ethylene glycol, ethylene glycol monomethyl ether, etc.; aromatic hydrocarbons such as toluene, benzene, xylene, etc.; hydrocarbons such as hexane, heptane, octane, etc.; tetrahydrofuran, diglyme, tetraglyme, and the like. They may be used as a single component or in combination of two or more types. Diglyme is preferable for film formation using spin coating. When diglyme or derivatives thereof is used, uniformity of a film produced is improved and also white turbidity of a film can be prevented. The amount of a solvent to dissolve or disperse a borazine-ring containing compound is not especially limited, and may be determined in response to production means of low dielectric materials. For example, for film formation using spin coating, a solvent type and the amount thereof may be determined so that viscosity suitable to spin coating is obtained.

A composition containing a borazine-ring containing compound is fed to a place desired, and solidified by drying. For example, to form an interlayer insulating film for semiconductor, it is coated on a substrate by spin coating and dried. When a coated film with desired thickness is not obtained by one coating and drying step, coating and drying may be repeated until desired thickness is attained. Film formation conditions such as rotation number of a spin coater, temperature for drying and time for drying are not especially limited.

Coating on a substrate may be performed using a method other than spin coating. For example, spray coating, dip coating, and the like may be used.

Then, a coated film is dried. Drying temperature of a coated film is usually from 100 to 250° C. Drying temperature here means maximum temperature in drying treatment. For example, when drying temperature is gradually increased and held at 100° C. for 30 minutes, followed by cooling, "drying temperature" is defined as 100° C. Drying temperature can be measured by a thermocouple. Drying time for a dried film is not especially limited. it may be determined as appropriate considering characteristics of a low dielectric material obtained, such as dielectric constant, humidity resistance, and the like.

EXAMPLES

1. Evaluation on Effect of Washing with Water and on the Repeated Number of Purification Example 1

Into a 3 L round bottom 5-neck flask, a monomethylamine-HCl salt (468 g; 6.931 mol) and chlorobenzene (2000 L) were charged. Into this flask, boron trichloride (870 g; 7.389 mol) was added drop-wisely over 20 hours, after taking out directly from a gas bomb, while liquidizing at −70° C. After the drop-wise addition, the reaction solution was matured at 135° C. for 60 hours to terminate synthesis reaction of B,B',B''-trichloro-N,N',N''-trimethylborazine (TCTMB).

After the reaction solution is cooled to 25° C., it was filtered and precipitate remained on a filter paper was washed. The filtrate was transferred to an egg-shaped flask, followed by solvent removal using an evaporator to obtain solid containing TCTMB. Solid yield was 145 g.

Into a 2 L 5-neck flask, TCTMB obtained (140 g) and diethyl ether (300 mL) as a solvent were charged. While controlling temperature inside a reaction system within 20 to 35° C., a diethyl ether solution (3 M, 800 mL) of a Grignard reagent, methyl magnesium bromide, was added drop-wisely over 5 hours, followed by refluxing and maturation for 3 hours to proceed a synthesis of hexamethylborazine. After the reaction solution is cooled to room temperature, it was filtered and concentrated to obtain solid A.

For solid A obtained, sublimation purification was performed once to obtain solid B. Solid B (7.59 g) thus obtained was dissolved in toluene, followed by transferring the toluene solution to a separatory funnel and washing with ion exchanged water (30 mL) three times. A toluene layer was taken out from the separatory funnel and solid C (7.58 g) was obtained by concentration. For solid C obtained, sublimation purification was performed twice to obtain hexamethylborazine (HMB). For HMB, impurity content was measured. The contents of chlorine atom and bromine atom were below detection limit, 1 ppm, and thus could not be determined. However, they are estimated to be far below 1 ppm. The content of magnesium was 0.02 ppm. The conditions of the sublimation purification and the results are shown in Table 1.

For measurement of impurity content in HMB, ion chromatography was used to measure halogen element content. And, for measurement of metal element content, an inductively coupled plasma emission spectrometer (IPC) was used. Measurement instrument and measurement conditions are as shown below.

[Ion Chromatography]

Halogen atom content was measured using "DX-500" from Japan Dionex Co., Ltd. "IonPacAS4A-SC" and "IonPacAG4A-SC" were used as a separation column and a guard column, respectively. As an eluent, 1.8 mmol/L $Na_2CO_3$ solution and 1.7 mmol/L $NaHCO_3$ solution were used. Flow rate of the eluent was set to be 1.5 ml/min. Charging amount of a sample was set to be 5 μL.

[ICP]

Metal element content was measured using "SPS4000" from Seiko Electronics Ind. Co., Ltd. Measurement was performed on a sample diluted in 10 times of methanol. Instrument setting values were: measurement wavelength=279.533 nm, high frequency output=1.80 kW and carrier gas (Ar) flow rate=0.6 L/min.

Example 2

For solid A obtained in Example 1, sublimation purification was repeated three times to obtain HMB. Impurity content in HMB was measured. The contents of chlorine atom and bromine atom were below detection limit, 1 ppm, and thus could not be determined. However, they are estimated to be far below 1 ppm. The content of magnesium was 0.03 ppm. The conditions of the sublimation purification and the results are shown in Table 1.

Comparative Example 1

For solid A obtained in Example 1, sublimation purification was repeated twice to obtain HMB. Impurity content in HMB was measured. The content of chlorine atom was 115.1 ppm and the content of bromine atom was not higher than 10 ppm. The content of magnesium was 0.61 ppm. The conditions of the sublimation purification and the results are shown in Table 1.

Comparative Example 2

For solid A obtained in Example 1, sublimation purification was performed only once to obtain HMB. Impurity content in HMB was measured. The content of chlorine atom was 152.8 ppm and the content of bromine atom was 7.1 ppm. The content of magnesium was 5.07 ppm. The conditions of the sublimation purification and the results are shown in Table 1.

TABLE 1

| | sublimation process | sublimation condition | impurities Cl | Br | Mg |
|---|---|---|---|---|---|
| example 1 | wash with water + sublimation (twice) | 90° C. 0.5 kPa | <1 ppm | <1 ppm | 0.02 ppm |
| example 2 | sublimation (three times) | 95° C. 0.4–0.5 kPa | <1 ppm | <1 ppm | 0.03 ppm |
| comparative example 1 | sublimation (twice) | 95° C. 0.4–0.5 kPa | 115.1 ppm | <10 ppm | 0.61 ppm |
| comparative example 2 | sublimation (once) | 95° C. 0.3–0.8 kPa | 152.8 ppm | 7.1 ppm | 5.07 ppm |

(Evaluation Result)

As are shown in Example 1 and Example 2, by a production method of the present invention, alkylborazine compound with quite low impurity content can be obtained.

In the cases of sublimation purification only once (Comparative Example 2) and sublimation purification twice (Comparative Example 1), certain high amount of halogen atoms and metals are contained. While, in the case of three times of sublimation purification (Example 2), contents of halogen atoms and metals are dramatically reduced.

In the case where washing with water is performed before sublimation purification, the contents of halogen atoms and metals are very low even in twice of sublimation purification. This is estimated due to improvement of efficiency in sublimation purification by decomposition of a halogenated borazine compound by washing with water.

Conditions in sublimation purification are a little different between in Examples and Comparative Examples, however, this is due to experimental errors.

2. Evaluation on the Repeated Number of Distillation Purification

Comparative Example 3

Into a 3 L round bottom 5-neck flask, a monomethylamine-HCl salt and chlorobenzene were charged. Into this flask, boron trichloride was added drop-wisely over 20 hours, after taking out directly from a gas bomb, while liquidizing at −70° C. After the drop-wise addition, the reaction solution was matured at 125 to 135° C. for 60 hours to terminate a synthesis reaction of B,B',B"-trichloro-N,N',N"-trimethylborazine (TCTMB).

After the reaction solution is cooled to 25° C., it was filtered and precipitate remained on a filter paper was washed. The filtrate was transferred to an egg-shaped flask, followed by solvent removal using an evaporator to obtain solid containing TCTMB.

Into a 2 L 5-neck flask, TCTMB obtained (175 g) and diethyl ether (300 mL) as a solvent were charged. While controlling temperature inside a reaction system within 20 to 25° C., a diethyl ether solution (3 M, 800 mL) of a Grignard reagent, ethyl magnesium bromide, was added drop-wisely over 5 hours, followed by refluxing and maturation for 3 hours to proceed a synthesis of B,B',B"-triethyl-N,N',N"-trimethylborazine (TETMB). After the reaction solution is cooled to room temperature, it was filtered and only ether was removed using an evaporator and concentrated.

For a solution remained, distillation was performed under reduced pressure only once to obtain TETMB (118 g, yield: 73.5%). The content of trialkylborane in TETMB after one-time distillation under reduced pressure was measured and found that 0.5 wt % of triethylborane was included. Results are shown in Table 2.

For measurement of trialkylborane in TETMB, gas chromatography-mass spectrometer (GC-MS) was used. Measurement instrument and measurement conditions are as shown below.

GC type: GC-17A model from Shimadzu Seisakusho Co., Ltd.

GC measurement conditions:
  Column DB-1 (J&W GC Column)
    Length=30 m, I.D.=0.25 mm, thickness=0.25 pm
  Sample room: 250° C.
  Detector: 280° C.
  Temperature increase condition
    Initial temperature=50° C., hold time=5 min.→increase rate=20° C./min. up to 250° C., hold time=15 min.→end MS type: QP-5000 model from Shimadzu Seisakusho Co., Ltd.

Ionization method: Electron impact (EI) method

Example 3

TETMB (107 g, yield: 65.7%) was obtained similarly as in Comparative Example 1, except that distillation under reduced pressure was added once more, that is, distillation under reduced pressure were performed twice. The content of trialkylborane in TETMB was measured and found that triethylborane content was below detection limit (1 ppm) of GC-MS. Results are shown in Table 2.

TABLE 2

|  |  | content of triethylborane |
| --- | --- | --- |
| comparative example 3 | distillation (once) | 0.5 wt % |
| example 3 | distillation (twice) | ≦1 ppm |

(Evaluation Result)

As shown in Comparative Example 3 and Example 3, by a production method of the present invention, alkylborazine compound with quite low content of trialkylborane can be obtained.

In the case of distillation purification only once (Comparative Example 3), certain amount of triethylborane generated was contained. While, in the case of twice of distillation purification (Example 3), the content of triethylborane was dramatically reduced.

What is claimed is:

1. A method for production of alkylborazine compound, comprising steps of:
  synthesizing an alkylborazine compound represented by the chemical formula 2 by a reaction of a halogenated borazine compound represented by the chemical formula 1 with a Grignard reagent; and
  washing the synthesized alkylborazine compound with water:

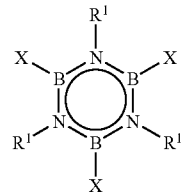

[chemical formula 1]

wherein $R^1$ independently represents alkyl group; and X represents halogen atom,

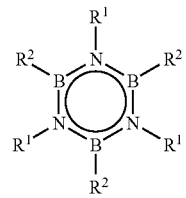

[chemical formula 2]

wherein $R^1$ independently represents alkyl group; and $R^2$ independently represents alkyl group.

2. A method for production of alkyl borazine compound, comprising steps of:
  synthesizing an alkylborazine compound represented by the chemical formula 2 by a reaction of a halogenated borazine compound represented by the chemical formula 1 with a Grignard reagent; and
  purifying the synthesized alkylborazine compound by sublimation purification or distillation purification at least three times:

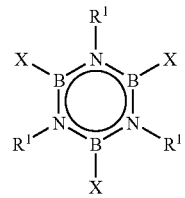

[chemical formula 1]

wherein $R^1$ independently represents alkyl group; and X represents halogen atom,

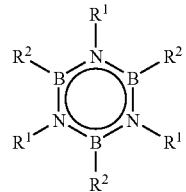

[chemical formula 2]

wherein $R^1$ independently represents alkyl group; and $R^2$ independently represents alkyl group.

3. A method for production of alkylborazine compound, comprising steps of:

synthesizing an alkylborazine compound represented by the chemical formula 2 by a reaction of a halogenated borazine compound represented by the chemical formula 1 with a Grignard reagent; and purifying the synthesized alkylborazine compound by distillation purification at least twice:

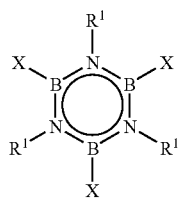

[chemical formula 1]

wherein $R^1$ independently represents alkyl group; and X represents halogen atom,

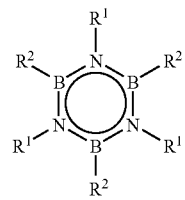

[chemical formula 2]

wherein $R^1$ independently represents alkyl group; and $R^2$ independently represents alkyl group.

4. A method according to claim 3, wherein the content of trialkylborane in the alkylborazine compound after completion of distillation purification is not higher than 1 ppm.

5. A method according to claim 2, wherein the synthesized alkylborazine compound is purified by sublimation purification at least three times.

6. A method according to claim 3, wherein the distillation purification is performed under reduced pressure.

7. A method according to claim 4, wherein the distillation purification is performed under reduced pressure.

* * * * *